(12) United States Patent
Josefsson (10) Patent No.: US 6,437,820 B1
(45) Date of Patent: Aug. 20, 2002

(54) MOTION ANALYSIS SYSTEM (75) Inventor: Thorleif Josefsson, Partille (SE)

(73) Assignee: Qualisys AB (SE)

( * ) Notice: Subject to any disclaimer, the term of this patent is extended or adjusted under 35 U.S.C. 154(b) by 0 days.

(21) Appl. No.: 09/350,853

(22) Filed: Jul. 9, 1999

Related U.S. Application Data (63) Continuation of application No. PCT/SE98/00049, filed on Jan. 13, 1998.

(30) Foreign Application Priority Data

Jan. 13, 1997 (SE) .............................. 9700067

(51) Int. Cl.$^7$ ............................... H04N 5/225
(52) U.S. Cl. ....................... 348/169; 345/156
(58) Field of Search ............... 348/169, 170, 348/154, 152, 155, 149, 148, 420, 158; 382/236, 168, 103; 340/572, 825.31, 5.8, 572.4; 600/595, 592; 356/620; 345/156, 158

(56) References Cited

U.S. PATENT DOCUMENTS

| | | | | |
|---|---|---|---|---|
| 4,813,436 A | * | 3/1989 | Au | .............. 600/595 |
| 5,459,793 A | | 10/1995 | Naoi | |
| 5,564,698 A | | 10/1996 | Honey | |
| 5,649,021 A | * | 7/1997 | Matey et al. | ............... 382/168 |
| 5,661,457 A | * | 8/1997 | Ghaffari et al. | ............. 340/572 |
| 5,708,423 A | * | 1/1998 | Ghaffari et al. | ........ 340/825.31 |
| 5,912,700 A | * | 6/1999 | Honey et al. | ............... 348/169 |
| 5,982,352 A | * | 11/1999 | Pyror | ....................... 348/158 |

FOREIGN PATENT DOCUMENTS

GB    2 237 699 A    5/1991

OTHER PUBLICATIONS

International Search Report; International Application No. PCT/SE 98/00049; May 20, 1998.
International Preliminary Examination Report, International Application No. PCT/SE98/00049; International Filing Date Jan. 13, 1998.

* cited by examiner

Primary Examiner—Chris Kelley
Assistant Examiner—Gims Philippe
(74) Attorney, Agent, or Firm—Lerner, David, Littenberg, Krumholz & Mentlik, LLP (57) ABSTRACT A motion analysis system for tracking the motion of one or more light-emitting markers attached to an object includes at least one camera for recording a series of image frames, and at least one light source in communication with said at least one camera for generating optical trigger signals. Each of the light-emitting markers includes a sensor for detecting the optical trigger signals generated by the at least one light source. Each light-emitting marker also includes one or more light-emitting elements for generating optical response signals after the sensor detects the optical trigger signals, the optical response signals having a first state and a second state being recordable by the camera as a series of image frames. The system also includes a detector for detecting the positions of the optical response signals in each recorded image frame, an arrangement mechanism for arranging the detected positions of the optical response signals in a sorted list, a processor for processing the sorted list and a generator for generating a unique identification code for each light-emitting marker based upon the optical response signals and the state of the response signals in the sorted list.

23 Claims, 5 Drawing Sheets

MOTION ANALYSIS SYSTEM

CROSS-REFERENCE TO RELATED APPLICATIONS

This is a continuation of International Application No. PCT/SE98/00049 filed on Jan. 13, 1998.

TECHNICAL FIELD OF THE INVENTION

The present invention relates to a motion analysis and/or tracking system including at least one camera unit and trackable markers. The camera unit includes emission detection means and being arranged for generating image frames substantially including activated marker, said markers comprise means for generating a response signal in response to a trigger signal detectable by said marker.

The invention also refers to method and an arrangement used for motion analysis and/or tracking.

BACKGROUND AND RELATED ART

Motion analysis is now a well-known method, using a camera unit and computer aid to analyse, e.g. bio-mechanics of human, animals or motions of a robot arm etc.

In a simple system markers are attached to the object to be analysed. In the past the object provided with the markers was first filmed and then manually analysed and digitalised to determine the correct position of the markers. This was a time-consuming procedure.

Presently, cameras equipped with so-called CCD plates are used. CCD plate, which is a light sensor, is generally arranged in communication with necessary optical elements. A CCD plate, consisting of lines of charged coupled sensors arranged as a matrix, i.e. arranged in an X and Y coordinate system, for one or several colours, converts the light (from the optical element) projected on it, by electronically scanning in Y direction each line of X sensors and producing a television (video) signal. Then, the signals may be analysed in different ways to detect the position of the markers attached to the object.

In many applications a body to be analysed is provided with several markers. One difficulty in these applications is to follow the motion of each individual marker.

Several suggestions have been made to solve this problem, for example by using markers having different colours. U.S. Pat. No. 5,459,793, teaches a system using several colour markers attached to the object to be analysed. Each marker has a high directive reflective member on a surface thereon, which reflects light having particular wave length. A colour TV camera receives the light reflected from the markers and outputs a colour image. A colour extraction unit is used, connected to the TV camera, extracts only a particular colour from the colour image. An area calculation unit connected to the extraction unit, calculates the area of the particular colour extracted by the colour extraction unit. A centre of gravity calculation unit calculates the position of gravity of the particular colour based on the area calculated by the area calculation unit.

Yet another arrangement is known through GB 2237699. This document describes a system of beacons and/or reflectors and cameras having CCD units. In case of coded beacons, identification coded bursts (ID code) of light emanating from a target are focussed onto the imagining portion of a CCD imager, which is initially operated in a capture mode wherein photo-generated charge pockets are serially scanned and transferred into a store section of the CCD. Each burst consists of an identification code followed by a tracking pulse. The store section contents of the CCD are read out to a processing unit looking for the presence of ID code burst. When an ID code is found, the CCD is operated in tracking mode in which only that photo-generated charge generated during the tracking pulse interval is transferred to the store section and charges generated during other times are dumped. The arrangement according to this invention uses several phases for tracking, i.e. target identification, image integration, frame transfer and image readout. A main drawback is that the image collection frequency is slowed down due to the processing phases. Another drawback is that if the photo-generated charges, e.g. from two different beacons bursting at same time are in same readout column or row (i.e. beacons are situated above each other or side-by-side) the ID code readout from the CCD will not be correct, which results in a defective tracking.

SUMMARY OF THE INVENTION

It is an object of the present invention to present a system that overcomes the problems related to tracking markers in real time in an inexpensive way. Yet another object of the invention is to provide a system in which several markers can be tracked and identified substantially simultaneously.

An advantage with the present invention is that camera exposure and marker identification can be carried out substantially simultaneously during same phase.

The objects are achieved by means of system according to the preamble, wherein each response signal has at least a first and a second state and the system further comprises means for detecting the positions of the response signals in each image frame, means for arranging said positions in a sorted set, means for processing the set of lists, and means for generating a unique identification code for each active marker based on the position of the response signals and state of the response signals.

Moreover, the invention relates to a method for tracking a marker device provided with a unique identity, in a motion analysis and/or tracking system including at least one camera unit, the method includes the steps of generating one or more trigger signals, detecting said trigger signal by said marker, generate a response signal by each marker according to instructions stored in each marker, detecting said response signal by the camera unit, generating a (sequential) code for each marker in respect of the response signals and positions of the same, and using said code for identifying each marker.

Other advantageous embodiments are characterized in the depending claims.

BRIEF DESCRIPTION OF THE DRAWINGS

In the following the invention will be described with reference to enclosed drawings, in which.

BASIC THEORY

Basically, an analogous system uses a conventional video signal from a camera as an input. By means of said signal the X and Y coordinates for the marker, which separate from the surroundings in intensity of light are calculated. The aim is to measure a movement of the marker as exact as possible, i.e. the inaccuracy, which is a result of the video signal consisting of a set of finite number of dots to be minimised.

The video signal consists of a number of lines, which are scanned in chronological order. A marker generates an image, which extends over one or several lines. By means of a comparator, it is possible to determine the start and the end of a marker section on a line may be determined. The marker image on a line is called a segment. The time is measured partly from the beginning of the line to the beginning of the segment ($X_s$) and partly from the beginning of the line to the end of the segment ($X_e$). The mean value of these two periods is a measure for the position of a segment in the space, in horizontal direction (if the lines are horizontal) while the serial number of the line (S) is a measure for position of the segment in the vertical direction. The length l of the segments is then $X_e$–$X_s$. The X and Y coordinates of the marker, $X_m$ and $Y_m$, respectively are obtained through formulas 1 and 2:

$$X_m = \frac{\sum \frac{(X_e - X_s) \cdot (X_e + X_s)}{2}}{\sum (x_e - X_s)} \quad (1)$$

$$Y_m = \frac{\sum ((X_e - X_s) \cdot S)}{\sum (x_e - X_s)} \quad (2)$$

The Σ sign indicates that the summation is carried out over all segments being a member of the marker image.

The above is applicable for an analogous signal. Similar calculations may be carried out, if image dots from a digital detector are transferred to another order than linear. There the centre points for all image elements that are members of the same marker are calculated. First, the image elements can be translated to lines and then the calculation may be carried out as in the analogous case.

The time points $X_s$ and $X_e$ can be measured with an electronic counting device connected to an oscillator. The counter starts in the beginning av the line and it is read when the start and end of a segment are reached. One problem is that the oscillator frequency, due to technical and economical reasons is limited. In the digital case the problem may be that the image elements cannot be as small as required.

To overcome this problem in analogues case a comparator is provided, which starts an integrator, which generates a linear potential slope, which starts from a potential $V_a$, to $V_b$ at time $X_s$. The slope is than sampled and measured when the counter changes between two values. The point when the slope passes a predetermined alteration value is used to define the time $X_s$. The difference between $X_s$ and $X_{ss}$ is a constant and it is determined by the integrator and the delays in the comparators. The time $X_{ss}$ is easily calculated from the measured points on the potential slope at the time for the change of the counter provided that at least two points on the slope are measured. For example, if two voltage values are measured, $V_1$ at $t_1$ and $V_2$ at $t_2$ and $V_0$ is between $V_1$ and $V_2$, $X_{ss}$ is interpolated by formula 3:

$$X_{ss} = t_1 + \frac{(t_2 - t_1) \cdot (V_0 - V_1)}{V_2 - V_1} \quad (3)$$

The time $X_e$ is measured in same way. In this embodiment a linear slope is used, because the calculations become simpler, however, other curves may be used.

In a preferred embodiment, the centre point x' of the marker is computed, using formula (4) and (5):

$$x' = \frac{\sum (l_k^n \cdot \bar{x}_k)}{\sum l_k^n} \quad (4)$$

$$y' = \frac{\sum (l_k^n \cdot S)}{\sum l_k^n} \quad (5)$$

where $l_k$ is the length of the segment k (i.e., $X_{ek}$–$X_{sk}$),
S is the serial number of the image element, and
$X_k$ is the centre of the segment k.

The $l_k$'s may then be stored in the memory unit for further calculations. For example, the area A of the image may be calculated using formula for area: $A=\Sigma l_k$. For a circular marker, it is possible to calculate the radius using $A=r^2 \cdot \pi$, which yields formula (7):

$$r = \sqrt{\frac{\sum l_k}{\pi}} \quad (7)$$

which may be computed in the computation unit.

The results are then transformed to an interface unit to further transmission to a computer unit in which the computed values, x' and r, can be used to show the position of each marker on a screen for simulation, positioning and other applications.

It is also possible to determine the three-dimensional position of the marker using above parameters, which will not be discussed closer here.

DETAILED DESCRIPTION OF AN EMBODIMENT

Figure 1:
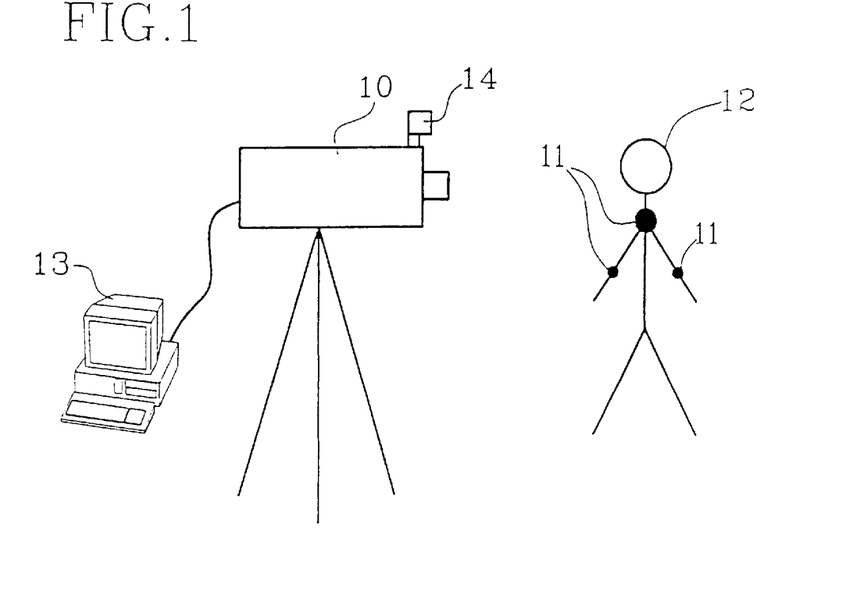
FIG. 1 is a schematic diagram of a simple motion analyse system according to the invention.

A simple schematic system according to the present invention is shown in FIG. 1. The system comprises at least one camera 10 directed to an object, in this case a human body 12, to be analysed and at least one marker 11 attached to the object 12.

The camera 10 may be connected to a computer device 13, to further processing of the signals received from the camera 10. The camera is also equipped with one or several light sources 14, such as a flash or searchlight. The light source may also be arranged somewhere else in the room, preferably connected to the camera 10.

In this embodiment the camera 10 is equipped with a CCD sensor. The camera 10 includes optical elements such as lenses and other focussing means (not shown) to project the image of a marking device 11 onto a CCD unit. The surface of the CCD unit is then scanned and the image signals including pixel information are converted to a suitable video signal by means of a converting unit, which may be integrated in the CCD unit. The video signal representing image lines, is then serially or in parallel sent to a processing unit. The processing unit digitalises the received video signal, for example using an A/D-converter. This signal may also be digitalised in a digitalizing unit. The processing unit may be connected to a memory unit, not shown, containing a set of instructions for controlling the processing unit.

In the following, references will be made to an embodiment operating in IR region, i.e. the camera "sees" bodies emitting infrared radiation.

Figure 2:
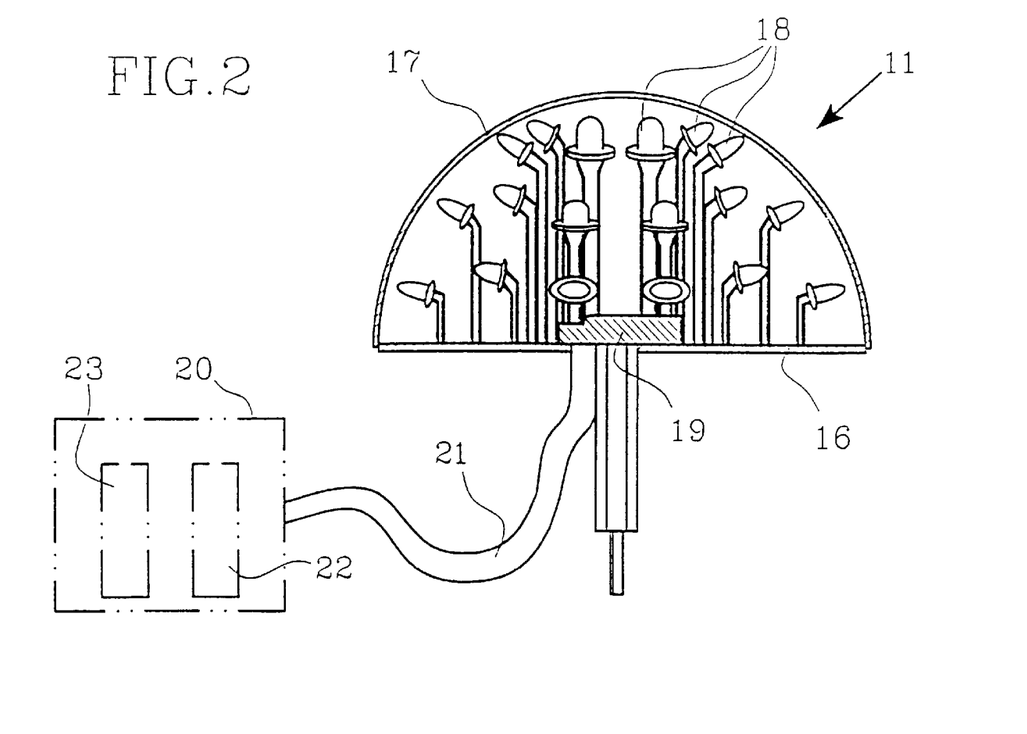
FIG. 2 schematically illustrates an embodiment of a marker according to the present invention.
Figure 3:
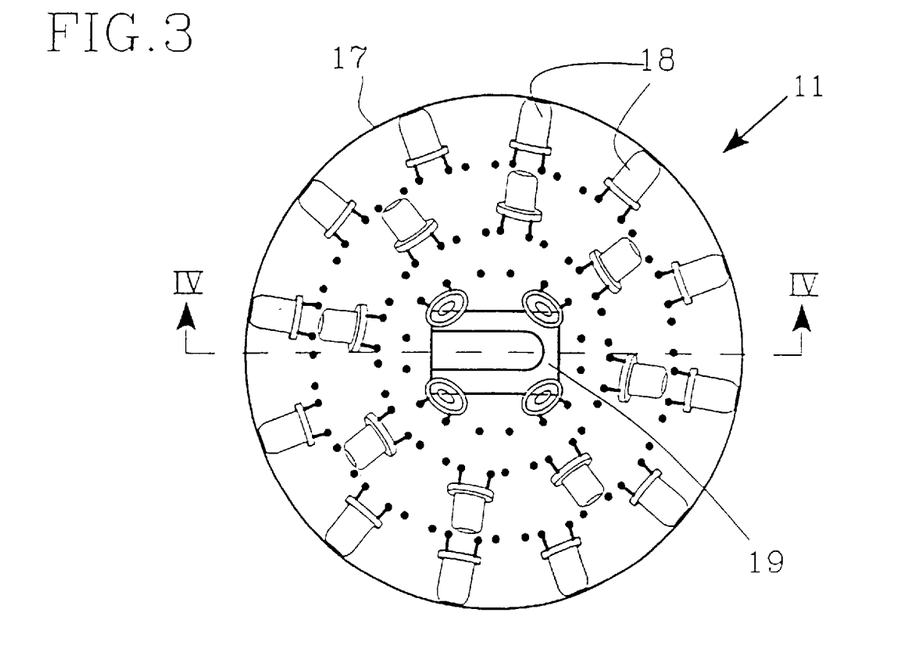
FIG. 3 is an elevation view, schematically showing the marker according to FIG. 2.
Figure 4:
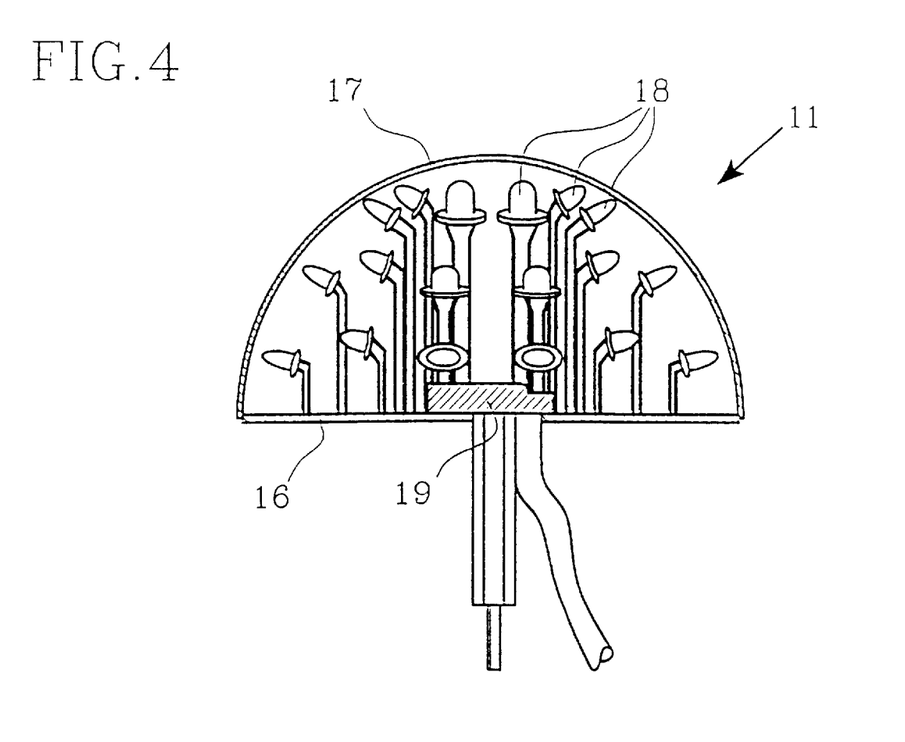
FIG. 4 is a cross section through the marker illustrated in FIG. 3 along line IV—IV.

An example of a substantially semispherical marker 11 is shown in FIGS. 2–4. Basically, the marker 11 consists of a supporting substrate 16 and a semispherical transparent cover 17. Inside the cover, several light-emitting means 18, such as LEDs (light-emitting Diodes), preferably IR-LEDs are arranged in a semispherical configuration. The marker 11 is also provided with a light sensor 19 in a substantially central position. The supporting substrate 16, which is a PCB of a suitable material is provided with conductors (not shown), interconnecting the LEDs 18, a control unit 20 and a power source (not shown) through a cable 21.

In contrast to known motion analyse systems the marker 11 is not arranged to reflect the light emitted by means of external light sources, but it is arranged to emit light by itself according to the following procedure.

The marker 11 is arranged to detect an incoming trigger signal, in this case, a light signal preferably in a special wave length, which is detected by the sensor 19. The detection of the trigger signal is then indicated to the control unit 20 by an internal signal. The control unit 20, which in its simplest form consists of a logic unit 22 and a driving circuit 23 for driving LED's 18 generates a response signal. The logic unit 22 may contain a unique identity number for each marker. It may also contain set of instructions for driving the LEDs. Integrating the sensor 19 and control unit 20 inside the marker 11 is of course possible.

Figure 5:
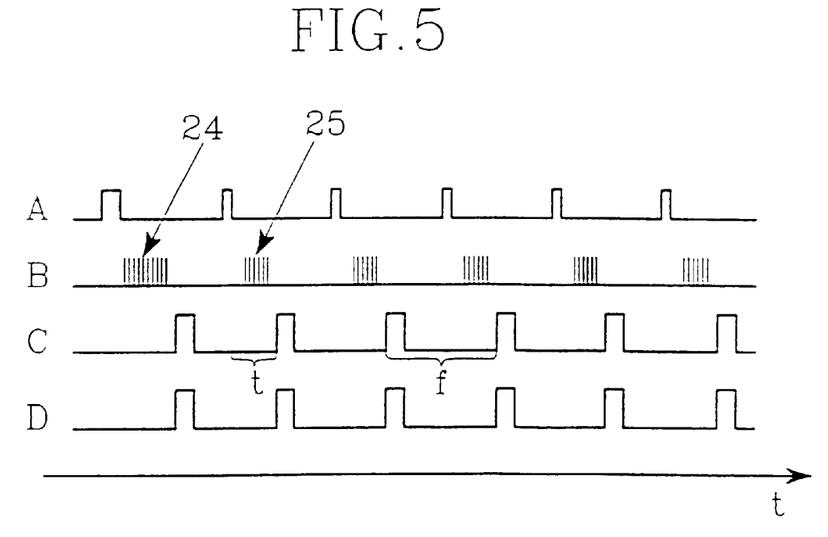
FIG. 5 schematically illustrates a timing chart for marker tracing according to the invention.

FIG. 5 is a schematic illustration of the timing schedule for signals in a preferred embodiment. The light source 14, controlled by the camera unit 10 periodically receives a signal A from the camera unit or other control means to output a trigger signal in form of a first and a second flash burst, 24 and 25, respectively, containing a number of flashes. The first burst 24, which preferably lasts longer than the second burst 25 is used to synchronise the counters of the markers and other cameras, if needed. Second, mainly shorter burst 25, is used as a trigger signal, substantially trigging all markers simultaneously to generate a response signal in form of a flash (or blink). Each response flash is shown as represented by signal peak on diagram B. Preferably, during each burst the diaphragm of the camera(s) is (are) closed, so that the light burst from the light source(s) 14 cannot be detected as an emitted light from the markers. After a predetermined delay time t, after a burst 24, 25, each marker outputs a response signal, substantially simultaneously, in form of a flash (light emission), if certain criteria are fulfilled. The cameras and markers are synchronised as illustrated in graphs C and D, where C shows the camera exposure time (peaks) and D shows the response signal (flash) from the markers. In graph C, a period f is between two exposures. In graph D each response signal corresponds to a bit, where the bit 1 is the first bit after the synchronization burst 24.

Figure 6:
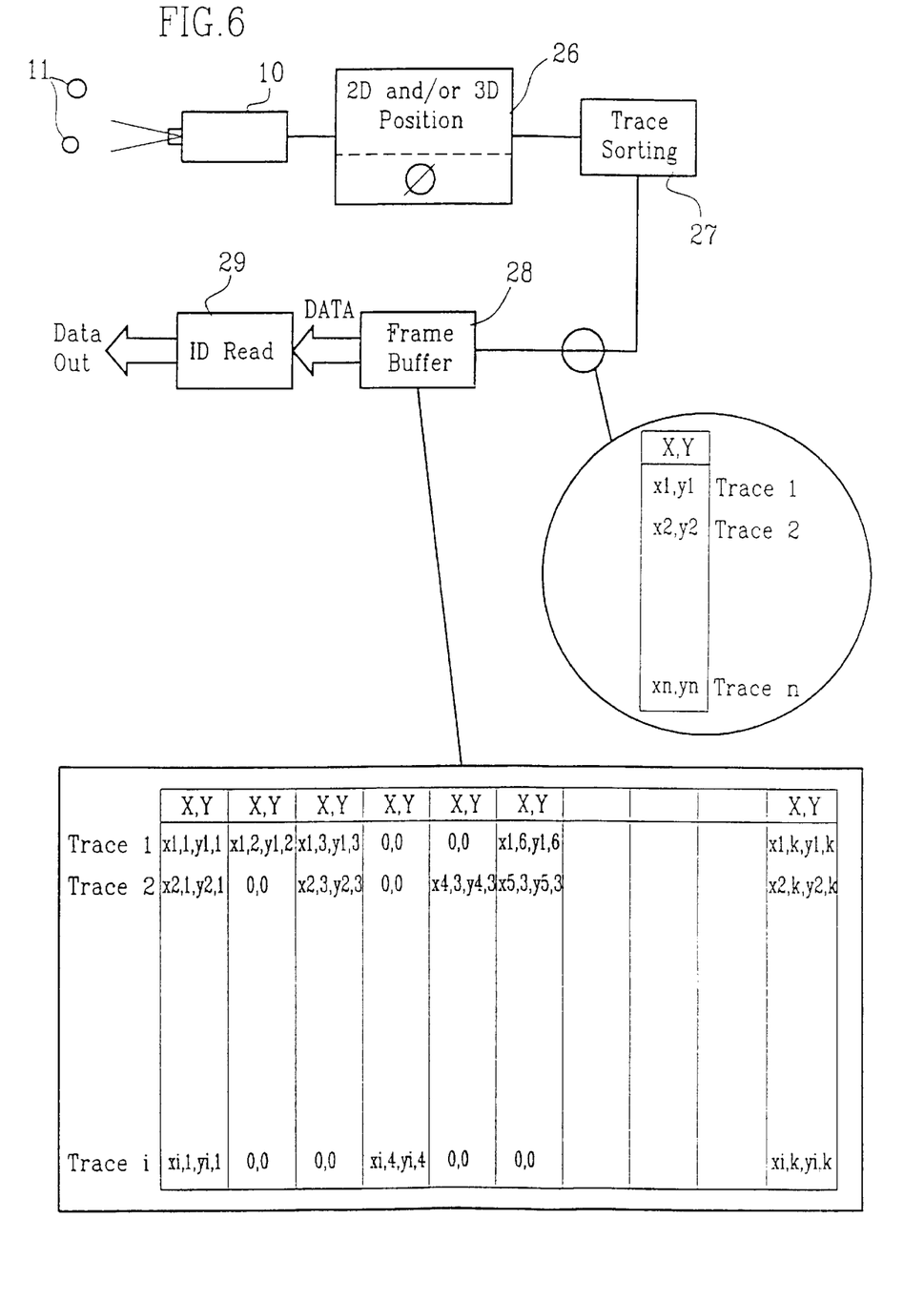
FIG. 6 is a schematic block diagram of a preferred system.

A block diagram of a preferred system according to the invention is schematically illustrated in FIG. 6. The system comprises the markers 11 attached to an object (not shown), the camera unit 10 and processing unit. The camera unit includes the CCD and means to transfer the signal readouts from the charged coupled sensors to the precessing unit. Each readout, i.e. CCD scan, comprises an image frame. The processing unit processes the incoming signal from the CCD and further comprises a position calculating device 26, sorting unit 27, buffering unit 28 and ID definition means 29. The position calculating device 26 is provided for calculating the two and/or three-dimensional position of each marker (image), according to formulas 5 and 6 above. It may also calculate the roundness of a marker. The sorting unit 27, e.g. including a memory unit, sorts the incoming positions (2D and/or 3D) of each marker in an image frame and generates a sorted list shown schematically in the encircled area on the drawing. Each row, so-called trace bit, of the list represents a position, denoted x, y, of a detected active marker. Preferably, the sorting order (first time) is from the first detected positions to last detected positions.

If a marker does not blink or it is hidden at least one position of the list will lack a correct position value. This position will be filed with zeros or another predetermined values. The lists are then transferred to the buffering unit 28, e.g. a FIFO memory unit, which buffers the incoming lists. The buffered lists form a trace table or a matrix, as shown in FIG. 6, the columns of which represent the lists received from the sorting unit and rows of the table show a sequence of lists, i.e. sorted positions of the detected markers. Data stored in each cell of the table may have the following form, $x_{i,k}, y_{i,k}$, where i is the number of markers used in a certain application and k is the number of columns, i.e. frames, a table contains.

The data in the frame table is then transferred to the ID definition unit for determination of the identity of each tracked marker, which will be described later.

The response flash from each marker is based on the instructions stored in the logic unit 22, in which also a unique identity number for each marker is stored. If a marker is "silent" no response signal is emitted. An active marker is preferably arranged to "blink" in same rate and phase that the cameras take a picture. By allowing an active marker to not respond according to a special, predetermined pattern it is possible to separate them from other active markers. The pattern the marker uses for generating a response signal, i.e. flash or not flash, is called the "sequence code". For simplicity 1 and 0 are used for describing the sequence code for each image frame the camera takes. 1 means that the marker has responded (flashed) in a frame and a 0 means that it has not. For example, 1110 means that the marker has blinked three times and has been silent once.

FIGS. 7a–7f show a series of schematic frames illustrating the movements of two markers 11A and 11B. For simplicity only two markers are used. The solid line circles are the markers blinking at a frame and dashed lined circles are illustrated to show the previous blinkings.

Figure 7A:
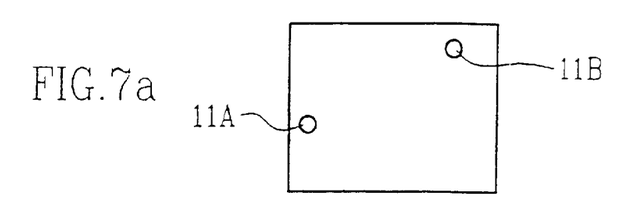
FIGS. 7a–7f are schematic views of frames according to the invention generated by a camera.
Figure 7B:
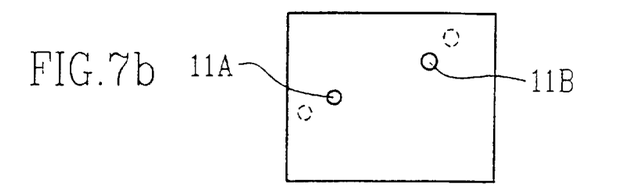
Figure 7C:
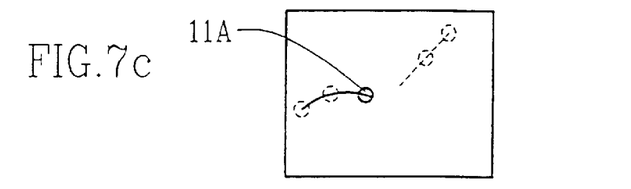
Figure 7D:
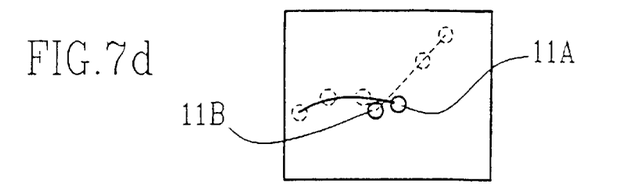
Figure 7E:
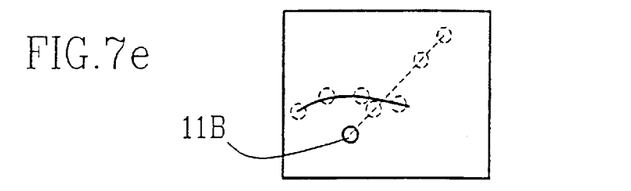
Figure 7F:
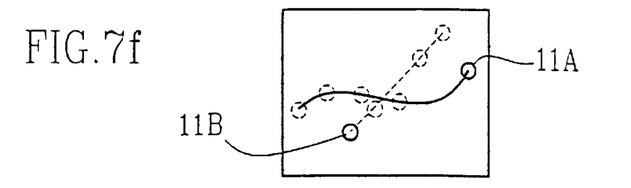

Assuming that after a synchronisation pulse, trigger pulses are emitted, in FIGS. 7a and 7b both markers blink. Here, it is assumed that both markers move but the method could be applied if only one or both markers are still. In FIG. 7c only marker 11A blinks. In FIG. 7d both markers 11A and 11B blink. In FIG. 7e only marker 11B blinks and in FIG. 7f both markers 11A and 11B blink. The frame series are terminated, for example by a new synchronisation pulse, after a predetermined number of trigger pulses, after a certain time duration, after that the buffer is filled etc.

To be able to insert the position data in a correct list position in a list, e.g. the trace sorting unit 27 may include a prediction unit for predicting the next displacement position of a marker using the previous position data. The predicted position data makes a basis for placing an incoming position data in a correct order.

Table I shows the frame table for the frames the buffer unit 28. For reason of simplicity, the detected positions are denoted by small letters.

TABLE I

| | x, y positions | | | | |
|---|---|---|---|---|---|
| Trace for marker 11A | a, b | c, d | e, f | g, h | 0, 0 | i, j |
| Trace for marker 11B | k, l | m, n | 0, 0 | o, p | q, r | s, t |

The positioned having 0,0 are the positions where the markers did not blink. This may occur either due to the sequential code of each markers, which count the bursts from the camera and stops blinking when a predetermined burst counter value occurs or because the marker is hidden and not detected by the camera.

The sequence codes for markers 11A and 11B are:

11A: 111101, and

11B: 110111.

Figure 7G:
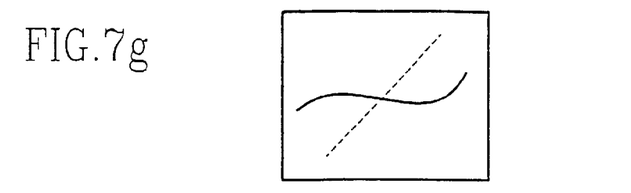
FIG. 7g is a schematic view of a trace generated according to the invention.

The sequence codes are processed in the ID definition unit 29. This unit contains data on which unique sequence code each marker is denoted with and by comparing the rows of the trace table obtained from the buffer 28 each marker may be provided with an identity, which in a computer may appear as different colours or the like. Trace rows for markers 11A and 11B are illustrated in FIG. 7g.

Usually, a set of codes that can not be confused no matter in which phase they occur in relation to each other needs a long code length. Shorter codes may be used if the markers always blink in phase. This is solved by using synchronizing pulses.

Each 1 or 0 in the sequence code will be called code bit, and each 1 for a marker pulse (a response signal) and each zero for no pulse. The length of a code is the number of code bits in a code, and the data loss for a certain code is defined as number of pulses failed to appear divided by the code length. The parity of the code is even if the number of non-appeared pulses in the code is even and odd if the same are odd. A set of codes is a set having same length, which can be used without confusion.

For increased reliability, several methods can be combined, e.g. parity control and zero-enclosing. Zero-enclosing means that it is not allowed to have two non-occurring pulses in a row. It yields two advantages, i.e. the tracking reliability will increase and partly a marker that is hidden for the moment, will not be mixed-up with a marker that sends a code, i.e. if it is not hidden only in one picture. Different grades of enclosing may be applied, for example grade 1 means that at least one marker pulse must bed obtained between each non-occurring marker pulse or grade 2 means that at least two marker pulses must bed obtained between each non-occurring marker pulse and so on. If the grade 3 is used, the 11011101 is allowable code but 1101101 is not.

Parity control increases the reliability more, if codes having same parity are used, instead of adding a parity bit, which is a conventional method.

When generating the set of codes, it is preferred to have a short code length and the total data loss should be as small as possible. Further, all codes in the set should have same parity.

Having data on the number of markers to be used in a certain application, the grade of zero-enclosure and maximum data loss grade a set of codes is generated. In the start the code length is set to a minimum. Based on the requirements and above data the parity and the size of the code set is calculated. Also, the total data loss may be calculated. When a sufficient code size is generated, the codes in the set are determined.

A counter in the logic unit of the marker counts the position of each bit in the identity binary code and a response signal is generated if the binary code for identity number of the marker is 1 (alternatively 0).

To eliminate the errors, the sequence code is tested according to the following principle, applied on the sequence code:

only one zero (0) [or one (1)] in series, odd number of zero (or one), selection of code for a certain degree of data disappearance (percentage of number of zeros or ones.)

If the result is approved, a marker is identified.

The code may naturally be completed by other criteria of different kind. This method makes it possible to detect a concealed marker in one or several frames as the trace bit will be missing if the marker is concealed.

In one embodiment, the markers may be provided with rechargeable batteries, whereby changing the identity number of each marker is possible, from application to application, when charging the batteries.

In respect of the "Basic Theory" part, herein above, the image elements may be arranged in lines by means of a low-pass filter to provide some continuos signal, which can be processed as the analogous signal. However, in the preferred embodiment each image element is measured individually and from the measured values, a value is interpolated, determining when a threshold T is passed, analogously to the Basic Theory part. In this case the integrator and the comparator are eliminated.

The digitalized-signal is then passed over to a comparison unit, which interpolates individual sample values about the predetermined threshold value, also called video level, which may be obtained from a memory unit. As described above, the object is to determine when the amplitude of the signal passes the value T. Each passage presents a start and stop coordinate of each segment with a high resolution, which can be about 30×number of pixels on a row. In a computation unit following calculation is executed:

$$X_{high\ resulotion} = Pixel\ No. + \frac{T - V_1}{V_2 - V_1} \quad (6)$$

Where $V_1$ and $V_2$ are the signal levels of preceding and succeeding pixels, respectively, received from the comparator unit.

Although, we have described and illustrated a preferred embodiment, the invention is not limited to said embodiment, variations and modifications may be made within the scope of the attached claims.

For example, the system may use other signalling arrangement, such as radio signals, laser beams or the like. The system may also use several types of light having different wave lengths. The marker may consist of a bulb or the like. Both camera and the light source may be connected to a control unit, remotely controlling the function of said parts.

Further, the form of the marker may vary due to the application area, for example it can be shaped as a trapezoid, cube, circular or the like.

The marker device may also include all parts, i.e. power source and the control unit. In case of radio signals a passive signalling arrangement may be used, which converts the electromagnetic signal to electrical voltage. Further, the shape of the marker may be changed to fit the application.

The markers can also include a programable control unit wich can be reprogrammed, e.g. the identity of a marker can be changed by modulating an identity code in a burst.

The system may also be used in several other application areas the motion analyses of a body, such as a tracking device, robot systems etc., well known for a person skilled in the art.

LIST OF DESIGNATION SIGNS

| 10 | Camera unit |
| 11 | Marker |
| 12 | Object |
| 13 | Computer |
| 14 | Light Source |
| 15 | Marker |
| 16 | Carrying substrate |
| 17 | Cover |
| 18 | LED |
| 19 | Sensor unit |
| 20 | Control unit |
| 21 | Cable |
| 22 | Logic unit |
| 23 | Driving circuit |
| 24 | Long burst |
| 25 | Short burst |
| 26 | Positioning unit |
| 27 | Sorting unit |
| 28 | Buffer unit |
| 29 | ID definition unit |

What is claimed is:

1. A motion analysis system for tracking the motion of one or more light-emitting markers attached to an object, said system comprising:
    at least one camera for recording a series of image frames;
    at least one light source in communication with said at least one camera for generating optical trigger signals;
    each said light-emitting marker including a sensor for detecting the optical trigger signals generated by said at least one light source, each said marker further including one or more light-emitting elements for generating optical response signals after the sensor detects the optical trigger signals, said optical response signals having a first state and a second state and being recordable by said camera as the series of image frames;
    said system further comprising means for detecting the positions of said optical response signals in each said recorded image frame, means for arranging the detected positions of said optical response signals in a sorted list, means for processing the sorted list and means for generating a unique identification code for each said light-emitting marker based upon the optical response signals and the state of the response signals in said sorted list.

2. A system according to claim 1, characterized in, that said markers are arranged to generate the response signal substantially simultaneously.

3. A system according to claim 1, characterized in, that each marker is arranged to generate a unique pattern of response signals, substantially repeated after a period.

4. A system according to claim 3, characterized in, that said period is between two synchronisation signal (24).

5. The system according to claim 1, wherein said trigger signal is a light burst generated by at least one light source according to a control signal.

6. The system according to claim 1, wherein said detecting means comprises a light sensor.

7. The system according to claim 1, wherein said means for radiating said response signal comprises a LED.

8. The system according to claim 1, wherein said system operates within an infrared region.

9. A system according to any of claims 1, characterized in, that said trigger signal and said response signals are electromagnetic waves.

10. An arrangement for tracking and identifying light-emitting markers comprising:
    at least one camera arranged to record a series of image frames;
    one or more light sources in communication with said at least one camera for selectively generating electromagnetic trigger signals;
    each said light emitting marker having a sensor for detecting the electromagnetic trigger signals generated by the one or more light sources and light-emitting elements for generating one or more light signals in response to the electromagnetic trigger signals; and
    a processing unit for processing the recorded series of image frames, said processing unit including means for utilizing the recorded image frames to calculate position data of said light-emitting markers, means for arranging the position data in a sorted order and sequentially outputting the sorted position data, means for generating a matrix including sequentially outputted sorted position data and an identification unit for processing each row of said matrix for generating a data sequence identifying each said light-emitting marker.

11. An arrangement according to claim 10, characterized in, that said markers are arranged with a control unit (20) to count number of trigger signals and avoid to generate a response signal in accordance with instructions of the control unit (20).

12. An arrangement according to claim 11, characterized in, that said response signals and said avoided response signals are represented by different data states (1;0) which constitute the identifying code.

13. An arrangement according to claim 11, characterized in, that said identification unit (28) includes means for transferring the identity codes to another processing unit.

14. An arrangement according to one of claims 11, characterized in, that said response signals are generated during entire exposure time of the camera unit.

15. An arrangement according to one of claims 10, characterized in, the arrangement further includes means for calculating the roundness of a marker.

16. An arrangement according to one of claims 10, characterized in, the markers are arranged to be programmed by means of electromagnetic waves.

17. A method for tracking the motion of a light-emitting marker comprising:
   providing said light-emitting marker including a sensor for detecting optical trigger signals and one or more light-emitting elements for generating optical response signals;
   generating one or more of said optical trigger signals;
   detecting said one or more optical trigger signals;
   after detecting said optical trigger signals, activating the one or more light-emitting elements of said marker to generate said optical response signals;
   recording said optical response signals;
   generating one or more lists for the recorded optical response signals; and
   utilizing the lists for the recorded optical response signals to generate a sequential code for said marker, wherein said sequential code identifies said marker.

18. A method according to claim 17,
characterized in,
that said response signal is an ON or OFF state for said marker.

19. A method according to claim 17,
characterized in,
that said OFF states determines a unique code useable to identify a marker.

20. A method according to claim 17,
characterized in,
that for increased code identification reliability parity control and/or zero-enclosing are used.

21. A method according to claim 20,
characterized in,
that a set of codes are generated using the maximum number of markers, a grade of zero-enclosure and a maximum data loss grade.

22. A method according to claim 17,
characterized in,
that said sequence code is tested according to the following principle, applied on the sequence code:
   only one zero (0) or one (1) in series,
   odd number of zero or one,
   selection of code for a certain degree of data disappearance (percentage of number of zeros or ones.).

23. A method according to a claims 17,
characterized in,
that all markers respond, substantially simultaneously.

* * * * *

UNITED STATES PATENT AND TRADEMARK OFFICE
CERTIFICATE OF CORRECTION

PATENT NO. : 6,437,820 B1
DATED : August 20, 2002
INVENTOR(S) : Thorleif Josefsson It is certified that error appears in the above-identified patent and that said Letters Patent is hereby corrected as shown below:

Column 1,
Line 14, "marker" should read -- markers --.

Column 2,
Line 12, delete "from".
Line 15, after "side)" insert -- , --.
Line 42, "generate" should read -- generating --.

Column 3,
Line 8, after "light" insert -- , --.
Line 15, delete "it is possible to determine".
Line 50, "av" should read therefor -- of --.
Line 59, "than" should read -- then --.
Line 62, "$X_s$" should read -- $X_{ss}$ --.

Column 4,
Line 8, after "in" insert -- the --.
Line 65, after "lines" delete ",".

Column 5,
Line 44, "trigging" should read -- triggering --.

Column 6,
Line 17, "The lists..." should start a new paragraph.
Line 18, "a" should read -- an --.

Column 7,
Line 1, after "frames" insert -- of --.
Line 37, after "pulses" insert -- that --.
Lines 50 and 52, "bed" should read -- be --.
Line 65, after "grade" insert -- of --.

Column 8,
Line 1, "is" should read -- are --.
Line 54, "arrangement" should read -- arrangements --.

UNITED STATES PATENT AND TRADEMARK OFFICE
CERTIFICATE OF CORRECTION

PATENT NO. : 6,437,820 B1
DATED : August 20, 2002
INVENTOR(S) : Thorleif Josefsson It is certified that error appears in the above-identified patent and that said Letters Patent is hereby corrected as shown below:

Column 9,
Line 2, "wich" should read -- which --.
Line 5, after "areas" insert -- of --.
Line 54, "A" should read -- The --.
Lines 55-56, "characterized in, that" should read -- wherein --.
Line 58, "A" should read -- The --.
Lines 59-60, "characterized in, that" should read -- wherein --.
Line 60, after "each" add -- said --.
Line 61, after "signals," add -- said response signals being --.
Line 63, "A" should read -- The --.
Lines 64-65, "characterized in that" should read -- wherein --.
Line 65, "signal" should read -- signals --.
Line 66, delete "(24)".

Column 10,
Line 10, "A" should read -- The --.
Line 10, "any of claims" should read -- claim --.
Lines 11-12, "characterized in, that" should read -- wherein --.
Lines 39, 45, 50, 55, 59 and 64, "An" should read -- The --.
Lines 40-41, "characterized in, that" should read -- wherein --.
Lines 41 and 44, delete "(20)".
Line 42, after "count", insert -- a --.
Line 42, "to generate" should read -- generating --.
Line 43, "of" should read -- from --.
Lines 46-47, "characterized in, that" should read -- wherein --.
Lines 48-49, "(1;0) which" should read -- that --.
Lines 51-52, "characterized in, that" should read -- wherein --.
Line 52, delete "(28)".
Lines 55, 59 and 64, "one of claims" should read -- claim --.
Lines 56-57, "characterized in, that" should read -- wherein --.
Lines 60 and 65, "characterized in," should read -- wherein --.

Column 11,
Line 19, "An" should read -- The --.
Lines 20-21, "characterized in, that" should read -- wherein each --.
Line 23, "A" should read -- The --.
Line 24, delete "characterized in,".

UNITED STATES PATENT AND TRADEMARK OFFICE
CERTIFICATE OF CORRECTION

PATENT NO. : 6,437,820 B1
DATED : August 20, 2002
INVENTOR(S) : Thorleif Josefsson It is certified that error appears in the above-identified patent and that said Letters Patent is hereby corrected as shown below:

<u>Column 12,</u>
Line 1, "that" should read -- wherein --.
Line 1, "determine" should read -- determines --.
Lines 3, 7, 13 and 21, "A" should read -- The --.
Lines 4-5, "characterized in, that for increased code identification reliability" should read -- wherein --.
Line 6, delete "and/".
Line 6, after "used" insert -- for increasing code identification reliability --.
Lines 8-9, "characterized in, that a set of codes for generating" should read -- further comprising the step of generating a set of codes --.
Lines 14-15, "characterized in, that" should read -- wherein --.
Line 18, after "one," add -- and --.
Line 20, delete "(percentage of number of zeros and ones.)".
Line 21, "a claims" should read -- claim --.
Lines 22-23, "characterized in, that" should read -- wherein --.
Line 23, after "all" insert -- the --
Line 23, after "respond" delete ",".

Signed and Sealed this

Eleventh Day of March, 2003

JAMES E. ROGAN
*Director of the United States Patent and Trademark Office*